US00PP19618P2

(12) United States Plant Patent
van den Dool

(10) Patent No.: US PP19,618 P2
(45) Date of Patent: Jan. 6, 2009

(54) ***×CUPRESSOCYPARIS* PLANT NAMED 'RECO'**

(50) Latin Name: *×Cupressocyparis leylandii*
Varietal Denomination: RECO

(76) Inventor: Pieter van den Dool, Goudserijweg 22, Boskoop (NL), 2771 AK ( * ) Notice: Subject to any disclaimer, the term of this patent is extended or adjusted under 35 U.S.C. 154(b) by 0 days.

(21) Appl. No.: 11/890,119

(22) Filed: Aug. 6, 2007

(51) Int. Cl.
*A01H 5/00* (2006.01)

(52) U.S. Cl. ..... Plt./213
(58) Field of Classification Search ..... Plt./213
See application file for complete search history.

*Primary Examiner*—Kent L Bell

(57) ABSTRACT

A new cultivar of ×*Cupressocyparis leylandii* named 'RECO' that is characterized by its upright, conical habit and dwarf size. In combination these traits set 'RECO' apart from all other existing varieties of ×*Cupressocyparis leylandii* known to the inventor.

1 Drawing Sheet

Genus: ×*Cupressocyparis.*
Species: *leylandii.*
Denomination: 'RECO'.

BACKGROUND OF THE INVENTION

The present invention relates to a new and distinct cultivar of ×*Cupressocyparis leylandii,* commonly known as Leyland Cypress. This plant is grown for use in the landscape as a specimen tree or hedge. The new cultivar is known botanically as ×*Cupressocyparis leylandii* and will be referred to hereinafter by the cultivar name 'RECO'.

'RECO' arose and was selected in 2001 by the inventor at the inventor's nursery in Waddinxveen, The Netherlands as naturally occurring single dwarf ×*Cupressocyparis leylandii* '2001' (not patented).

The new variety 'RECO' is a shrub characterized by its slow growth and dwarf size. 'RECO' has a conical upright form that at 6 or 7 years is approximately 1.5 meters in height.

The closest known comparison plant known to the breeder is the parent plant ×*Cupressocyparis leylandii* '2001'. The parent plant is typical of the species and grows rapidly to heights of nearly 70 m if not pruned. Unlike its parent, 'RECO' grows at a slower rate and after 6 or 7 years has not exceeded 1.5 m in height while maintaining the positive characteristics of denseness and attractive fragrance.

The first asexual reproduction of 'RECO' was conducted by the inventor in 2001 using softwood cuttings. The inventor has since determined that 'RECO' reproduces true to type in all successive generations of asexual reproduction.

An application for a grant of European Plant Breeders Rights for 'RECO' has been filed as application number 2004/2428 on May 27, 2005. The application is pending at the European Plant Breeder Rights Office. The inventor released his first plants to the public in March 2007.

SUMMARY OF THE INVENTION

The following traits have been repeatedly observed and represent the characteristics of 'RECO'. These traits in combination distinguish 'RECO' from all other varieties of ×*Cupressocyparis leylandii* known to the inventor. 'RECO' has not been tested under all possible conditions and phenotypic differences may be observed with variations in environmental, climatic and cultural conditions, without however, any difference in genotype.

1. 'RECO' has an upright, conical habit.
2. 'RECO' has a slow growth rate and reaches 1.5 m after 6 or 7 years of growth.
3. 'RECO' is hardy in USDA Zones 6–9.

BRIEF DESCRIPTION OF THE DRAWING

The accompanying color drawing illustrates the overall appearance of the new cultivar 'RECO' showing the colors as true as it is reasonably possible to obtain in colored reproductions of this type. Colors in the photographs may differ from the color values cited in the detailed botanical description, which accurately describe the actual colors of the new variety of 'RECO'.

The drawing labeled as FIG. 1 illustrates a 6 year old plant of 'RECO' growing in open ground in Waddinxveen, The Netherlands.

BOTANICAL DESCRIPTION OF THE PLANT

Figure 1:
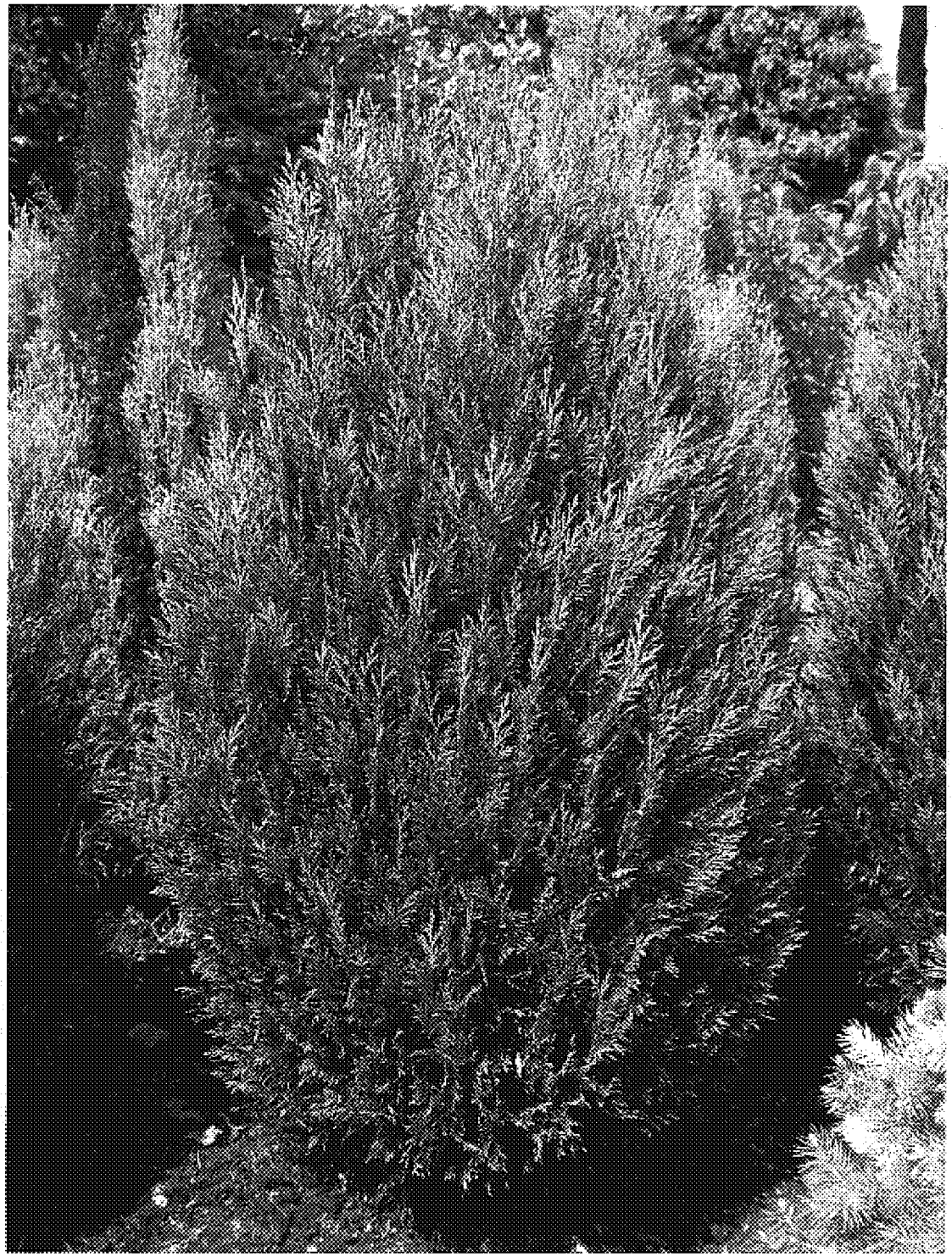

The following is a detailed description of 'RECO'. Botanical data was collected during the 2006 growing season from plants which were approximately three years old in a 6.5 liter container. The observed plants were growing in an unheated glass greenhouse in Nikerk, Netherlands. The color determinations have been made by reference to the 2001 edition of The Royal Horticultural Society Colour Chart, except where general color terms of ordinary dictionary significance are used.

Family: Cupressaceae.
Botanical classification: ×*Cupressocyparis leylandii.*
Genus: ×*Cupressocyparis.*
Species: *leylandii.*
Variety Denomination: 'RECO'.
Common name: Leyland cypress.
Use: Landscape shrub or hedging plant.

Container size: Suggested container sizes for planting: 1, 3, 5 or 7 gallon.

Cultural requirements: Moist, well drained fertile soils.

Light requirement: Full sun to partial shade.

Parentage: ×*Cupressocyparis leylandii* '2001'.

Plant description:

*Plant habit.*—Upright and conical

*Vigor.*—Moderate.

*Dimensions after 6 years (in the field).*—1.5 m in height and 40 cm in width.

*Dimension of the observed plant (3 years old).*—An average of 64 cm in height and 29.8 cm in width.

*Growth rate.*—Approximately 20 cm per season in a young plant.

*Hardiness.*—At least USDA zone 6–9.

*Vigor.*—Moderate.

*Root system.*—Shallow, fibrous

Propagation: Propagation is accomplished by softwood, semi hardwood, or hardwood cuttings. It is recommended that the cuttings are taken when the cutting stem is brown in color.

*Time to develop roots.*—From 6 to 8 weeks to initiate roots.

*Temperature for rooting.*—Rooting occurs when rooting medium is maintained within temperature range 18° C. to 28° C.

*Hormone.*—It is recommended to apply a rooting hormone in the form of a powder or dip. The hormone Indole 3- butyric acid (known as IBA) is an effective rooting agent and may be applied in a concentration of 0.8% (8,000 parts per million).

*Crop time.*—An established plant in a 1 gallon container takes an average one year to finish.

*Disease and pest susceptibility.*—'RECO' is neither less nor more susceptible to pests or diseases than the species or in comparison to other cultivars of the species known to the inventor.

Branches:

*Branching habit.*—Main stems grow from base and have lateral branches.

*Basal branching.*—Yes.

*Number of lateral branches.*—An average of 23.

*Lateral branch dimensions.*—An average of 37.4 cm in length and 3 mm in diameter.

*Internode length.*—An average of 1.1 cm.

*Stem.*—Appearance: Rounded, covered with scale-like leaves, dull. Aspect: Rounded, covered with scale-like leaves. Strength: Strong. Color: Young twigs 141B and 141C; older bark 200D; where young twigs change to older bark, stems are 151B and 151C. Pubescence: None.

Foliage:

*Arrangement.*—Opposite.

*Quantity of leaves per lateral branch.*—Over 7,500 scale-like leaves.

Leaf:

*Quantity of leaflets per leaf.*—Not applicable.

*Shape.*—Scale-like; elliptic.

*Tip.*—Acute.

*Base.*—Cuneate.

*Dimensions.*—An average of 4 mm in length and 1 mm in width.

*Texture.*—Moderately glossy.

*Pubescence.*—None.

*Margin.*—Entire.

*Venation.*—None visible.

*Color, young leaf (adaxial).*—143A.

*Color, young leaf (abaxial).*—143A and 143B.

*Color, mature leaf (adaxial).*—141B.

*Color, mature leaf (abaxial).*—141B and 141C.

*Attachment.*—Sessile.

Durability to stress: Very high.

Stipules, tendrils, thorns, spines or prickles: none.

Fragrance: When crushed, resinous, typical of ×*Cupressocyparis leylandii.*

Flowers: No flowers have been observed.

Seeds: No seeds have been observed.

What is claimed:

1. A new and distinct cultivar of ×*Cupressocyparis* plant named 'RECO', as described and illustrated here within.

* * * * *